United States Patent
Trembley et al.

(10) Patent No.: US 10,905,584 B2
(45) Date of Patent: Feb. 2, 2021

(54) INDIRECTLY COOLED CRYOTHERAPY APPARATUS AND METHOD

(71) Applicant: Air Products and Chemicals, Inc., Allentown, PA (US)

(72) Inventors: Jean-Philippe Trembley, Surrey (GB); Patrick Viroux, Zoersel (BE); Ivo Johannes Hendrikus Tiemessen, Amsterdam (NL)

(73) Assignee: Air Products and Chemicals, Inc., Allentown, PA (US)

(*) Notice: Subject to any disclaimer, the term of this patent is extended or adjusted under 35 U.S.C. 154(b) by 128 days.

(21) Appl. No.: 16/091,313

(22) PCT Filed: Apr. 3, 2017

(86) PCT No.: PCT/US2017/025705
§ 371 (c)(1),
(2) Date: Oct. 4, 2018

(87) PCT Pub. No.: WO2017/176621
PCT Pub. Date: Oct. 12, 2017

(65) Prior Publication Data
US 2019/0151140 A1 May 23, 2019

Related U.S. Application Data

(60) Provisional application No. 62/453,670, filed on Feb. 2, 2017, provisional application No. 62/317,953, filed on Apr. 4, 2016.

(51) Int. Cl.
*A61F 7/00* (2006.01)
*G16H 20/40* (2018.01)

(52) U.S. Cl.
CPC .......... *A61F 7/0053* (2013.01); *A61F 7/0085* (2013.01); *G16H 20/40* (2018.01);
(Continued)

(58) Field of Classification Search
CPC ...... A61F 7/0053; A61F 7/0085; G16H 20/40
See application file for complete search history.

(56) References Cited

U.S. PATENT DOCUMENTS

| 4,784,140 A | * | 11/1988 | Donnerback | F25D 3/102 607/83 |
| 5,077,980 A | * | 1/1992 | Weber | A61F 7/00 128/DIG. 27 |

(Continued)

FOREIGN PATENT DOCUMENTS

| DE | 84 32 906 U1 | 6/1987 |
| DE | 94 19 997 U1 | 2/1995 |

OTHER PUBLICATIONS

European International Search Report and Written Opinion of the International Searching Authority, dated Jun. 30, 2017, for PCT/US2017/025705.

*Primary Examiner* — Christopher A Flory
(74) *Attorney, Agent, or Firm* — Larry S. Zelson

(57) ABSTRACT

A cryotherapy apparatus including a heat exchanger, a cryotherapy chamber, cryogenic nitrogen supply and exhaust conduits to and from the heat exchanger, an air return conduit to flow warmed air from the cryotherapy chamber to the heat exchanger, an air supply conduit to flow chilled air from the heat exchanger to the cryotherapy chamber, a variable speed fan to cause flow of air through a loop including the air supply and return conduits, the heat exchanger, and the cryotherapy chamber, and a controller programmed to control the flow rate of air by regulating the speed of the variable speed fan according to a treatment protocol; and a method of delivering cryotherapy according to a customized treatment protocol taking into account one or more of: a patient's treatment goals, a customization factor, a personalization factor, and an adaptation factor.

16 Claims, 6 Drawing Sheets

(52) U.S. Cl.
CPC .................. *A61F 2007/0064* (2013.01); *A61F 2007/0069* (2013.01); *A61F 2007/0086* (2013.01); *A61F 2007/0093* (2013.01); *A61F 2007/0096* (2013.01)

(56) References Cited

U.S. PATENT DOCUMENTS

| | | | | |
|---|---|---|---|---|
| 5,692,495 A * | 12/1997 | Sheu | ...................... | A61K 33/00 128/203.12 |
| 2009/0277445 A1 * | 11/2009 | Markwart | .............. | B64D 13/00 128/203.12 |
| 2012/0059364 A1 * | 3/2012 | Baust | ..................... | A61B 18/02 606/24 |
| 2013/0253491 A1 * | 9/2013 | Burr | .................. | A61B 18/0218 606/21 |
| 2014/0277302 A1 * | 9/2014 | Weber | .................. | A61F 7/0085 607/104 |
| 2014/0364777 A1 * | 12/2014 | Swyer | .................. | A61H 9/0057 601/11 |
| 2016/0038213 A1 * | 2/2016 | Maners | .............. | A61B 18/0218 606/21 |
| 2016/0089262 A1 | 3/2016 | Kuehne | | |

* cited by examiner

INDIRECTLY COOLED CRYOTHERAPY APPARATUS AND METHOD

CROSS-REFERENCE TO RELATED APPLICATIONS

This application claims the priority of U.S. Provisional Application No. 62/317,953, filed on Apr. 4, 2016, and U.S. Provisional Application No. 62/453,670, filed on Feb. 2, 2017, each of which is incorporated by reference herein in its entirety.

BACKGROUND

An apparatus and methods are described herein for providing customized cryotherapy treatments using an indirectly cooled single-occupancy cryotherapy device or multi-person cryotherapy chamber.

Whole-body cryostimulation/cryotherapy (WBC) is a non-invasive technique characterized by relatively short bursts of cold (−90° C. to −140° C.) for about 2-4 minutes to the body periphery (i.e., exposed skin surface area) that provoke and harness reactions to cold, causing various physiological reactions that may promote healing and recovery.

Existing single-person cryotherapy devices, or cryosaunas, include a chamber where a patient stands inside with the patient's head protruding above the top of the cryosauna. In previously-existing devices, cooling is typically provided directly by liquid nitrogen (LIN) (or occasionally by liquid air, if available), wherein the vaporized LIN, which is now very cold nitrogen gas (GAN), comes into direct contact with the patient. First, the LIN flows into a LIN reservoir mounted behind or beneath the chamber, where it is vaporized immediately, and then the very cold GAN is flowed into the chamber.

Typically, the GAN flow is driven by the gas expansion caused by the vaporization. However, in some cases, a blower or fan is used to circulate the GAN. The very cold GAN thus provides the cooling for the patient. The temperature is controlled to prevent the vaporized nitrogen from getting too cold for the patient, and protection is also provided to prevent LIN carryover into the chamber, although the possibility for entrained droplets of LIN does exist.

Each patient can usually adjust his or her position inside of the chamber to ensure that the head is above the cold nitrogen atmosphere. This is typically accomplished by a height adjustable side wall, a movable standing platform, or something simple like a box.

These existing cryosaunas are very similar across all suppliers, and all suffer from similar performance difficulties. The primary difficulty is that the temperature within the chamber is often considerably different from top to bottom of the chamber, sometimes by as much as 70° C. when controlling to a set point of −135° C. (e.g., −150° C. at the bottom and −80° C. at the top). This temperature gradient is does not provide for consistent and well-controlled cryotherapy treatments; a more homogeneous exposure temperature (evenness of cold) is preferred. A secondary difficulty is the possible safety (i.e., asphyxiation) hazards of exposure of a patient to high concentrations of nitrogen, as well as the potential cold burns caused by entrained LIN droplet contact with a patient.

In addition, implementing cryotherapy stimulation preferably requires adequate protocol settings, in particular related to safety, due to the extreme cold conditions to which the individuals are exposed, but also to produce beneficial therapeutic results. It is known that there is considerable between-subject variability in skin cooling responses to WBC, and as patients and athletes feature a wide variety of anthropometric and morphological body characteristics, a one-size-fits-all strategy appears to be inadequate regarding the safety and efficacy of the treatment. See Hammond, L. E., Cuttell, S., Nunley, P., Meyler, J., *Anthropometric characteristics and sex influence magnitude of skin cooling following exposure to whole body cryotherapy*, Biomed. Res. Int. 2014, 628724, which is incorporated herein by reference in its entirety. The skin temperature response of individuals with a higher adiposity is faster and more pronounced compared to thinner individuals thereby affecting their safety and the treatment efficacy.

As described herein, the well-validated Fiala thermal Physiology and Comfort numerical simulation model has been utilized for cryotherapy applications to assess the impact of personal characteristics on the skin cooling responses and stimulation settings in relation to safety and efficacy. See Fiala, D., Lomas, K. J., Stohrer, M., 1999, *A computer model of human thermoregulation for a wide range of environmental conditions: the passive system*, J. Appl. Physiol. 87, 1957-1972; and Fiala, D., Havenith, G., 2016, *Modelling human heat transfer and temperature regulation*, In: Gefen, A., Epstein, Y. *The Mechanobiology and Mechanophysiology of Military-Related Injuries*. Springer International Publishing, Cham: 265-302, which are each incorporated herein by reference in their entirety.

SUMMARY

Aspect 1. A cryotherapy apparatus comprising: a heat exchanger mounted in an exchanger enclosure; a cryotherapy chamber configured to receive at least a portion of a body of a patient designated to receive cryotherapy; a nitrogen supply conduit configured to supply cryogenic nitrogen to the heat exchanger; a nitrogen exhaust conduit configured to exhaust nitrogen from the heat exchanger; an air return conduit configured to flow warmed return air from the cryotherapy chamber to the heat exchanger enclosure; an air supply conduit configured to flow chilled air from the heat exchanger enclosure to the cryotherapy chamber; a variable speed fan configured to cause a flow rate of chilled air through a loop including the air return conduit, the heat exchanger, the air supply conduit, and the cryotherapy chamber; and a controller programmed to control the flow rate of chilled air to the cryotherapy chamber by regulating the speed of the variable speed fan according to a treatment protocol.

Aspect 2. The cryotherapy apparatus of Aspect 1, wherein the fan is a reversible fan configured to enable a flow rate of chilled air through the loop in either direction.

Aspect 3. The cryotherapy apparatus of Aspect 1 or Aspect 2, further comprising a control valve in the nitrogen supply conduit to regulate the supply of cryogenic nitrogen, wherein the controller is further programmed to control the supply of cryogenic nitrogen according to a treatment protocol.

Aspect 4. The cryotherapy apparatus of any one of the preceding Aspects, wherein the controller is further programmed to selectively direct the chilled air to one or more selected portions of the body of a patient designated to receive cryotherapy, and to control the flow rate of the chilled air to the one or more selection portions of the human body.

Aspect 5. The cryotherapy apparatus of any one of the preceding Aspects, further comprising a temperature sensor positioned to sense a return air temperature, wherein the controller is further programmed to control the flow rate of air based at least on part on the return air temperature.

Aspect 6. The cryotherapy apparatus of any one of the preceding Aspects, further comprising a condensate drain positioned at a low point in the air return conduit for removing condensation formed in one or both of the exchanger enclosure and the cryotherapy chamber.

Aspect 7. The cryotherapy apparatus of any of the preceding Aspects, further comprising a temperature sensor to sense a nitrogen exhaust temperature, wherein the controller is further programmed to shut off liquid nitrogen supply if the nitrogen outlet temperature is at or below a preset limit.

Aspect 8. The cryotherapy apparatus of any of the preceding Aspects, further comprising a heater in the air return conduit for heating the recirculating air to enable defrosting of the cryotherapy chamber.

Aspect 9. The cryotherapy apparatus of any of the preceding Aspects, wherein the controller is further programmed to provide customized treatment protocols based one or more of: a characteristic of the patient being treated, a type of treatment required, a type of injury being treated, a type of athletic activity from which recovery is desired, and a portion of the body requiring treatment.

Aspect 10. The cryotherapy apparatus of Aspect 9, wherein the controller is programmed to provide customized treatment protocols taking into account a patient's treatment goals.

Aspect 11. The cryotherapy apparatus of Aspect 9 or Aspect 10, wherein the controller is programmed to provide customized treatment protocols taking into account a customization factor based one or more of a patient's susceptibility to cold, age, and athletic type.

Aspect 12. The cryotherapy apparatus of any one of Aspects 9 to 11, wherein the controller is programmed to provide customized treatment protocols taking into account a personalization factor based on one or more of a patient's body height, mass, surface area, body surface area-to-mass ratio, body fat percentage, lean body mass, body mass index, and fat free mass index.

Aspect 13. The cryotherapy apparatus of any one of Aspects 9 to 12, wherein the controller is programmed to provide customized treatment protocols taking into account a and an adaptation factor based on one or both of treatment frequency and a treatment cycle.

Aspect 14. The cryotherapy apparatus of Aspect 9, wherein the customized treatment protocols enable customization of a portion of the body being treated, exposure times, timed cycles, exposure temperatures, temperature cycles, cold intensity, and cold intensity cycles.

Aspect 15. The cryotherapy apparatus of Aspect 9, wherein the controller is programmed to provide customized treatment protocols taking into account one or more of: a patient's treatment goals, a customization factor, a personalization factor, and an adaptation factor; wherein the customization factor takes into account one or more of a patent's cold susceptibility, a patient's age, and a patient's athletic type; wherein the personalization factor takes into account one or more of a patient's body height, mass, surface area, body surface area-to-mass ratio, body fat percentage, lean body mass, body mass index, and fat free mass index; and wherein the adaptation factor takes into account a one or both of treatment frequency and a treatment cycle.

Aspect 16. The cryotherapy apparatus of any one of Aspects 9 to 15, wherein the controller is programmed to provide customized treatment protocols by calculating one or more of the patient's treatment goals, the customization factor, the personalization factor, and the adaptation factor based on a reference athlete.

Aspect 17. The cryotherapy apparatus of any of the preceding Aspects, wherein the chilled air flow rate is controlled to provide a treatment temperature from −150° C. to −90° C.

Aspect 18. The cryotherapy apparatus of any of the preceding Aspects, wherein the chilled air flow rate is controlled to provide a treatment temperature from −135° C. to −110° C.

Aspect 19. The cryotherapy apparatus of any of the preceding Aspects, wherein the chilled air flow is controlled to provide a heat transfer effect from 5 W/m2° C. to 100 W/m2° C.

Aspect 20. A method of delivering cryotherapy using a cryotherapy chamber configured to receive at least a portion of a human body designated to receive cryotherapy, the method comprising: recirculating air in a loop through a heat exchanger, into the cryotherapy chamber, and out form the cryotherapy chamber, and returning to the heat exchanger; chilling the air to a therapeutic chilled air temperature in the heat exchanger by heat exchange with liquid nitrogen; and operating the cryotherapy chamber according to a customized treatment protocol comprising controlling the flow rate of the chilled air.

Aspect 21. The method of Aspect 20, operating the cryotherapy chamber according to a customized treatment protocol further comprising: selectively directing the chilled air to one or more selected portions of the body of a patient designated to receive cryotherapy; and controlling the flow rate of the chilled air to the one or more selection portions of the human body.

Aspect 22. The method of Aspect 20 or Aspect 21, further comprising: controlling the flow rate of the chilled air based on one or more of: a characteristic of the patient being treated, a type of treatment required, a type of injury being treated, a type of athletic activity from which recovery is desired, and a portion of the body requiring treatment.

Aspect 23. The method of Aspect 22, further comprising: selectively directing the chilled air to the one or more selected portions of the body designated to receive cryotherapy based on one or more of: a characteristic of the patient being treated, a type of treatment required, a type of injury being treated, a type of athletic activity from which recovery is desired, and a portion of the body requiring treatment.

Aspect 24. The method of Aspect 23, further comprising customizing the treatment protocol to vary one or more of: a portion of the body being treated, exposure times, timed cycles, exposure temperatures, temperature cycles, cold intensity, and cold intensity cycles.

Aspect 25. The method of any one of Aspects 20 to 24, further comprising customizing the treatment protocol to take into account a patient's treatment goals.

Aspect 26. The method of any one of Aspects 20 to 25, further comprising customizing the treatment protocol to take into account a customization factor based one or more of a patient's susceptibility to cold, age, and athletic type.

Aspect 27. The method of any one of Aspects 20 to 26, further comprising customizing the treatment protocol to take into account a personalization factor based on one or more of a patient's body height, mass, surface area, body surface area-to-mass ratio, body fat percentage, lean body mass, body mass index, and fat free mass index.

Aspect 28. The method of any one of Aspects 20 to 27, further comprising customizing the treatment protocol to take into account a and an adaptation factor based on one or both of treatment frequency and a treatment cycle.

Aspect 29. The method of any one of Aspects 20 to 24, further comprising: taking into account one or more of: a patient's treatment goals, a customization factor, a personalization factor, and an adaptation factor; wherein the customization factor takes into account one or more of a patent's cold susceptibility, a patient's age, and a patient's athletic type; wherein the personalization factor takes into account one or more of a patient's body height, mass, surface area, body surface area-to-mass ratio, body fat percentage, lean body mass, body mass index, and fat free mass index; and wherein the adaptation factor takes into account a one or both of treatment frequency and a treatment cycle.

Aspect 30. The method of any one of Aspects 22 to 29, further comprising calculating one or more of the patient's treatment goals, the customization factor, the personalization factor, and the adaptation factor based on a reference athlete.

Aspect 31. The method of any one of Aspects 20 to 30, further comprising: controlling the flow rate of the chilled air based at least in part on the temperature of the air returning to the heat exchanger.

Aspect 32. The method of any one of Aspects 20 to 31, further comprising: draining condensate from the loop.

Aspect 33. The method of any one of Aspects 20 to 32, further comprising: controlling the chilled air flow rate to provide a chilled air temperature from −150° C. to −90° C.

Aspect 34. The method of Aspect 33, further comprising: controlling the chilled air flow rate to provide a chilled air temperature from −135° C. to −110° C.

Aspect 35. The method of any one of Aspects 20 to 34, further comprising: controlling the chilled air flow to provide a heat transfer effect from 5 W/m2° C. to 100 W/m2° C.

BRIEF DESCRIPTION OF THE DRAWINGS

The present invention will hereinafter be described in conjunction with the appended figures wherein like numerals denote like elements.

DETAILED DESCRIPTION

Described herein is an indirectly cooled single-occupancy cryotherapy device or cryotherapy chamber where chilled air is re-circulated through a therapy chamber and re-cooled by a cryogen heat exchanger to provide a more even temperature distribution within the chamber from top to bottom. In addition, the chilled air flow is controlled so that the amount of cooling (cold intensity) can be adjusted to suit specific patient requirements, including but not limited to the individual physical characteristics of the patient, and an integrated controller enables customized treatment protocols to be applied. For example, treatment protocols can be customized depending on the type of condition being treated (e.g., fatigue, sleep, recovery, injury), and can be modified based on the characteristics of the patient (e.g., gender, size, height, weight, skin type). The cold treatment provided can also be adjusted by controlling the speed of the air flow through the chamber at one or more locations to vary the heat transfer effect onto the skin and/or across various parts of the patient's body.

In one embodiment of an indirectly cooled single-occupancy cryotherapy device, the re-circulating air flow can be adjusted to provide a desired height cooling curtain over the patient within the therapy chamber, including an optional automatic adjustment to suit the patient's height. By using the adjustable-height cooling curtain, the type of cryotherapy treatment can be customized, for example to target only the lower body, only the upper body, another partial portion of the body, or even the entire body (i.e., whole body cryotherapy (WBC) or partial body cryotherapy (PBC)).

Cooling is provided by liquid nitrogen (LIN), but the nitrogen can never come into contact with the patient and is vented safely to atmosphere. The LIN is used to cool air by way of a LIN-air heat exchanger, and the chilled air is recirculated through the therapy chamber and re-cooled in a loop. A specially-designed heat exchanger allows for any moisture to be collected in the cold surfaces of the exchanger without reducing the cooling performance of the exchanger during its normal operating cycle.

In a further embodiment, a heater may be installed in the recirculation air flow to clean and defrost the therapy chamber after use, allowing water to be drained safely from the chamber and not leaving any reside in the patient area. This cleaning and defrosting ability helps to ensure consistent performance of the apparatus.

Figure 1:
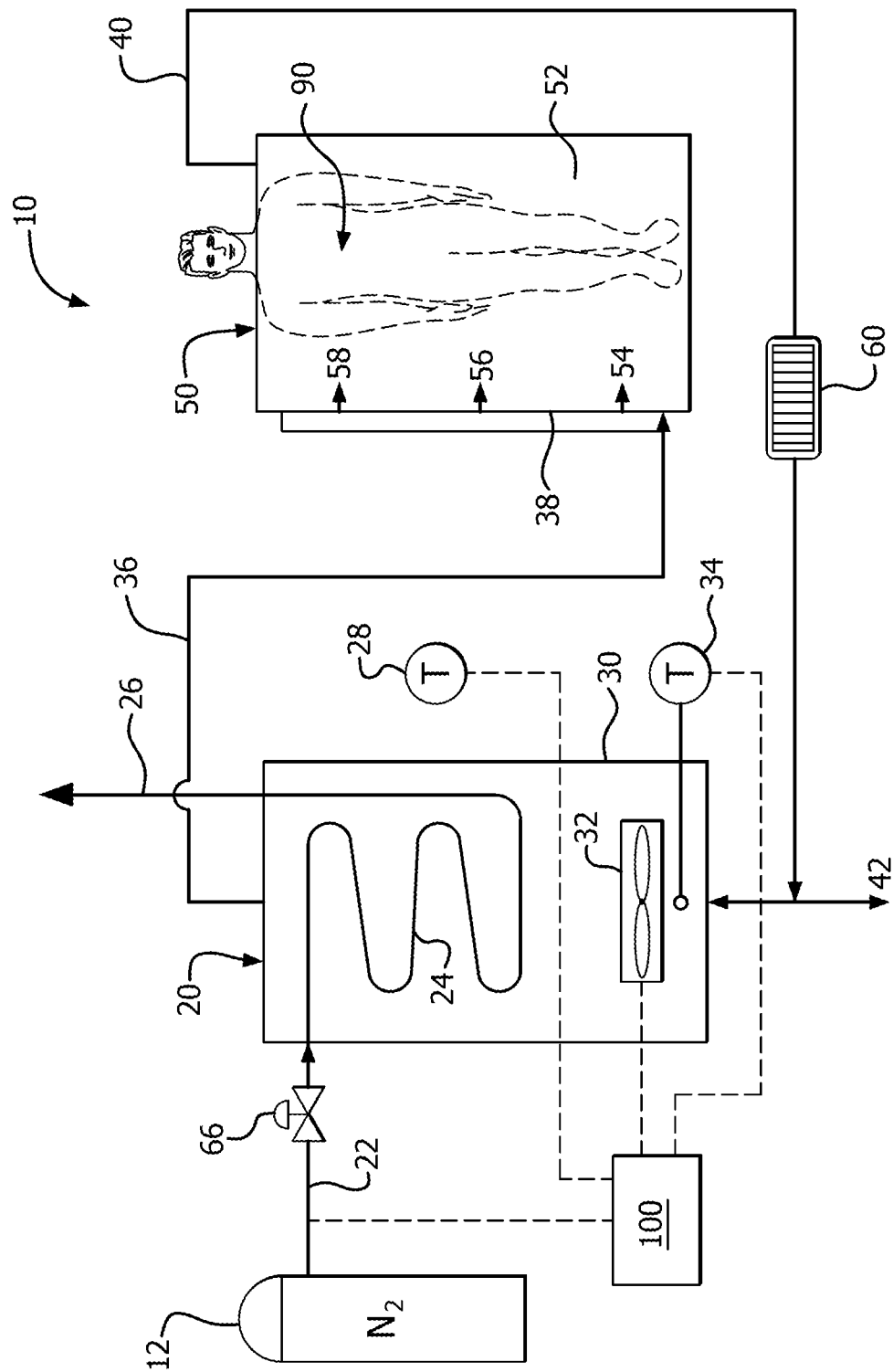
FIG. 1 is a schematic showing an embodiment of an indirectly cooled cryotherapy apparatus.

An embodiment of an indirectly-cooled cryotherapy apparatus 10 is shown in FIG. 1. The apparatus 10 includes an exchanger enclosure 20 configured to use liquid nitrogen to chill recirculating air and a therapy chamber 50 configured to receive a patient's body 90 designated to receive cryotherapy. The exchanger enclosure 20 and the therapy chamber 50 may be contained in a single physical structure, or may be two separate structures connected by the air supply conduit 36 and the air return conduit 40.

During operation of the apparatus 10, air is recirculated in a nearly closed loop through the exchanger enclosure 20 where it is chilled by heat exchange with vaporizing liquid nitrogen and through the therapy chamber 50 where it is warmed by contact with a patient's body. As discussed further below, the air may be recirculated in either direction, depending on the application.

The exchanger enclosure 20 houses a heat exchanger 24. A liquid nitrogen source 12 supplies liquid nitrogen to the heat exchanger 24 via a nitrogen supply conduit 22. Gaseous nitrogen (which was vaporized during the heat exchange process) is exhausted to vent from the heat exchanger 24 via a nitrogen exhaust conduit 26. In the depicted embodiment, a variable speed fan 32 is positioned in the exchange enclosure 20 below the heat exchanger 24 to provide an upward flow of recirculating air across the heat exchanger 24. The fan 32 may be reversible to allow for recirculation of air in either direction. Recirculated air enters a lower portion of the enclosure 20 below the fan 32 through an air return conduit 40, flows upward through the fan 32 and then through the heat exchanger 24, and exits an upper portion of the enclosure 20 above the heat exchanger 24 through an air supply conduit 36. The fan 32 can be alternatively positioned above the exchange enclosure 20 to provide further flexibility and flow control of the recirculating air.

The air supplied in the air supply conduit 36, which is the therapeutic chilled air, has been chilled by the heat exchanger 24 to be cooler than the air recirculated by the air return conduit 40. The temperature of the therapeutic chilled air supplied to the therapy chamber 50 via the air supply conduit 36 is preferably as cold as or colder than −90° C. and is more preferably as cold or colder than −110° C. and as cold as −135° C. for optimal cryotherapy treatment effects. Typically, the chilled air is not colder than −150° C. Alternatively or in addition to controlling the therapeutic chilled air temperature, the cold intensity may be controlled. Cold intensity is defined as the net heat transfer effect of the treatment on a patient's body, and takes into account both the chilled air temperature and the air velocity flowing through the chamber and/or across the patient's body (which correlates to the heat transfer coefficient). Preferably, the cold intensity is at least 5 $W/m^{2o}$ C. and no greater than 100 $W/m^{2o}$ C., and more preferably the cold intensity is from 10 $W/m^{2o}$ C. to 50 $W/m^{2o}$ C.

The therapy chamber 50 receives chilled air from the air supply conduit 36 into a distribution manifold 38 having at least one nozzle configured to supply chilled air to an interior 52 of the chamber 50. In the depicted embodiment, three different nozzle locations are provided for supplying air from the manifold 38, including a first nozzle 54 for supplying chilled air to a lower portion of the chamber interior 52, a second nozzle 58 for supplying chilled air to an upper portion of the chamber interior 52, and a third nozzle 56 for supplying chilled air to an intermediate portion of the chamber interior 56, it being understood that any number and location of nozzles may be used to enable the chamber 50 to provide targeted and customized cryotherapy to various parts of the patient's body. In addition, nozzles can be positioned all on one side of a patient's body, or at any point around the chamber surrounding the patient's body. Individually controlled baffles or valves (not shown) may be provide so that each nozzle can be turned on or off, or modulated, during all or a portion of each cryotherapy treatment session.

Warmed air from the therapy chamber 50, having passed over the patient's body thereby taking on heat, is drawn out of an upper portion of the therapy chamber 50 through the air return conduit 40. It is understood that because of the non-sealed nature of the therapy chamber 50, the recirculating air operates in a nearly closed but slightly open loop; while a small percentage of the chilled air provided by the air supply conduit 36 may escape from the chamber 50, a commensurate amount of make-up or fresh air will be drawn into the air return conduit 40 to maintain a substantially consistent amount of recirculating air flow for a given speed of the variable speed fan 32. Also, provisions can be made to remove moisture from the recirculating air as necessary.

Alternatively, chilled air can be flowed from the heat exchanger 24 into an upper portion of the therapy chamber 50 through the air return conduit 40, and then drawn into the nozzles 52, 54, and 56 for return to the heat exchanger 24 via the manifold 38 and the air supply conduit 36 (reverse flow operation), which may be advantageous for certain types or modes of therapy, and would provide a further option for customization of treatment protocols. This can be accomplished by a second fan (not shown) or by making the fan 32 reversible, or by valves or dampers or other similar mechanisms.

Operation of the cryotherapy apparatus 10 is controlled by a specially-programmed controller 100. A temperature sensor 34, or multiple temperature sensors 34 with the values averaged or selectively combined in a weighted or non-weighted formula, detects a recirculating air temperature and provides that temperature to the controller 100. The temperature sensor 34 may be mounted in a lower portion of the exchanger enclosure 20 upstream of the fan 32 as shown, or it may be positioned in the air return conduit 40. In one embodiment, the controller 100 is programmed to control the recirculating air temperature within a predetermined treatment range by regulating the speed of the fan 32, and thus controlling the recirculating air flow rate.

In another embodiment, a control valve 66 is provided in the liquid nitrogen supply conduit 22, and the controller 100 is further programmed to control the recirculating air temperature by regulating the control valve 66 to control the flow of liquid nitrogen into the heat exchanger 24, by itself or in combination with the speed of the variable speed fan 32.

A temperature sensor 28 may also be provided to detect a nitrogen exhaust temperature in the nitrogen exhaust conduit 26 to enable the controller 100 to perform a safety shutdown if the nitrogen exhaust temperature drops below a predetermined value.

In another embodiment, a heater 60 is provided in the air return conduit 40 to enable the chamber 50 to be defrosted and cleaned periodically and/or between uses. A low-point drain 42 may be provided in the air return conduit 40 to enable removal of condensate that drains into the air return conduit 40 from the exchanger enclosure 20 and/or the therapy chamber 50.

In another embodiment the controller 100 can be programmed to provide various treatment protocols to suit the type of patent treatment required. These pre-programmed treatment protocols are developed using scientific studies to ascertain the optimal cryotherapy treatment conditions, taking into account one or more parameters specific to a patient being treated. These parameters may include, without limitation, the size, shape, and weight of the patient, the portion of the body to be treated (e.g., a specific part or region, or the whole body), a specific injury or injury type to be treated, a specific sport or athletic activity from which the patient is recovering, the frequency of treatments, etc. These treatment protocols will include parameters for cold intensity, treatment exposure time, and treatment temperature, with an operator or the patient having the ability to select the requited protocol depending on the patient conditions.

Although the embodiment described herein relates to a single person single-occupancy cryotherapy apparatus and method, the same features can be applied a single person or multi-person whole body cryotherapy chamber indirectly cooled by LIN, where at least one patient is completely enclosed with the whole body exposed to the cold cryotherapy treatment conditions using chilled air as described herein.

Given the considerable between-subject variability in skin cooling under whole-body cryostimulation/cryotherapy (WBC), a simulation study was performed to assess the impact of personal characteristics, following a stepwise approach. The Fiala thermal Physiology and Comfort numerical simulation model (FPC model) was adapted for cryotherapy settings and as an initial step was validated against published averaged data. The FPC model was then further calibrated to individual body and skin temperature responses observed from six patients during WBC exposures in a single-person WBC Unit 10 as described above. The FPC model was then used to simulate skin temperature responses to 3 minute WBC exposure at −110° C. for 65 female and male patient configurations with varying anthropometric and morphological body characteristics. The results indicated that while the skin temperature response was always fast, it was also very sensitive to variations in personal settings. These variations and sensitivities were captured by the individualized FPC numerical simulation model. Body fat content and the fat free mass index were found to significantly affect the personal skin temperature response and thus those parameters also affect the protocol settings for WBC in the cryotherapy unit 10, both with regard to safety and therapeutic cooling efficacy.

To ensure sound basis for customized cryotherapy protocols, the FPC model was first validated using published skin response data under WBC exposure, followed by calibrating the numerical simulations specifically to WBC exposures carried out in a single-person WBC Unit. Calibrated simulations were then employed to study the influence of personal characteristics on WBC responses.

Figure 2:
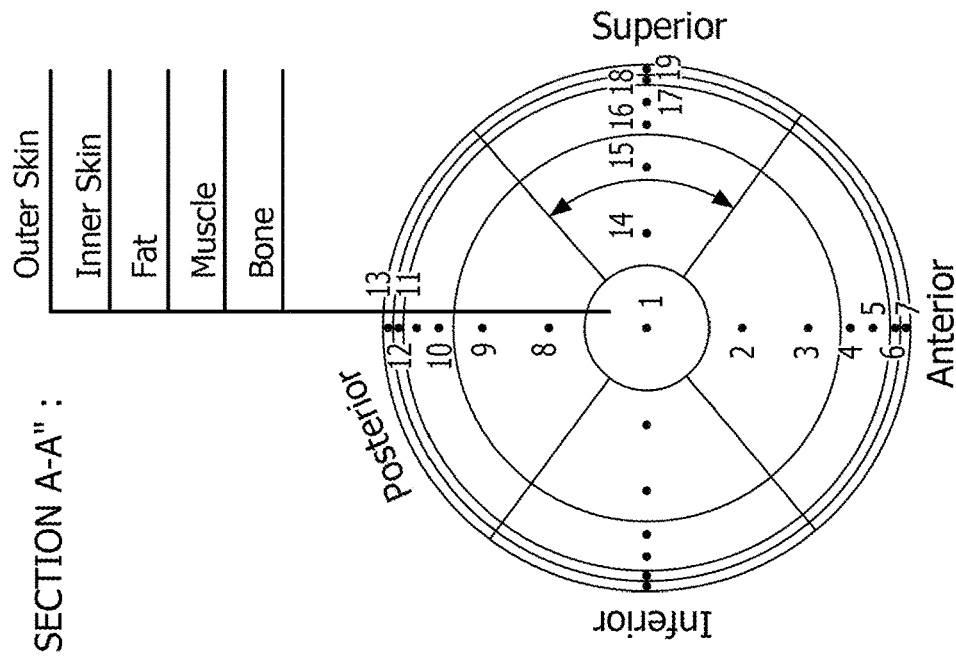
FIG. 2 is a schematic showing a passive system model for thermal stimulation.
Figure 2:
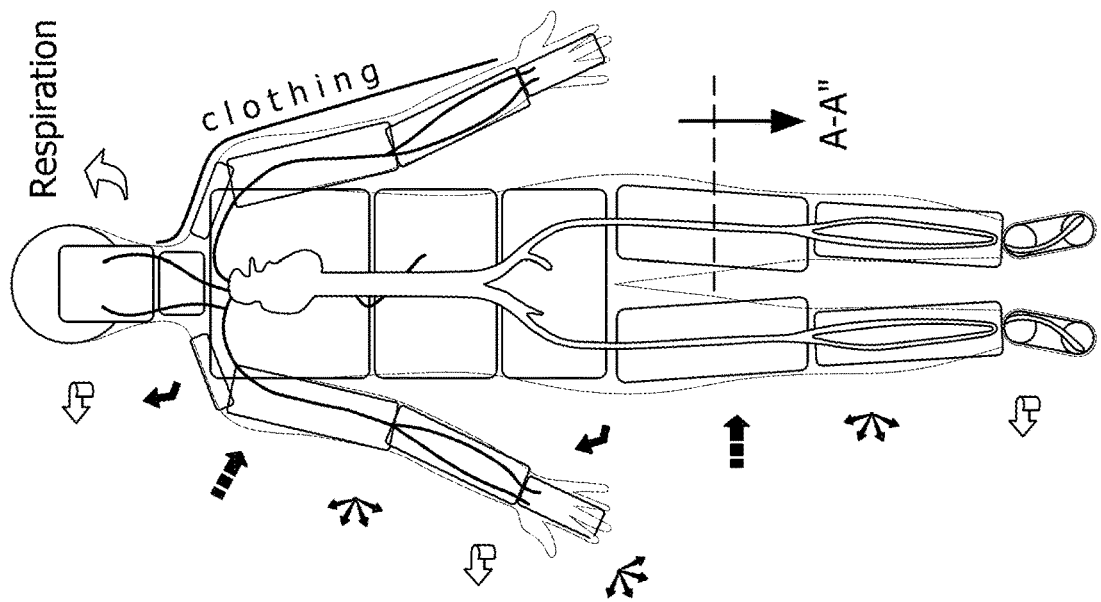

The FPC model consists of two interacting systems: an controlling active system and an controlled passive system. The passive system simulates the human body and the dynamic heat and mass transfer occurring within the body and at its surface (FIG. 2). The active system is a cybernetic model predicting the thermoregulatory responses of the human central nervous system.

The FPC passive and active systems were individualized to account for personal variations in body height, mass, fat content, age, gender, physical fitness, and acclimatization status. The individualized or personalized model contains a scalable human anthropometry and morphology model, and an individual heat stress response model to predict body temperature and regulatory responses of male and female subjects covering a wide range of personal characteristics. The FPC model was adapted and used to predict body core and skin temperature responses of male and female subjects to whole body cryostimulation/cryotherapy.

Initially, the FPC mode was validated for WBC applications against published averaged skin cooling data from experiments conducted by Hammond. The main objective of the Hammond study was to quantify the sex-specific differences in skin temperatures of subjects undergoing a WBC exposure to −110° C. After 20 min adaptation to 21.6±1.6° C. (mean±SD), 18 males (age 29.5±4.4 years, height 179.2±6.2 cm, weight 80.6±9.4 kg, body fat percentage 15.6±4.9%) and 14 females (age 28.3±6.4 years, height 164.6±6.5 cm, weight 64.1±12.4 kg, body fat percentage 27.4±8.8%) were exposed to a WBC protocol consisting of 30 second exposure to −60° C. followed by 2 minutes at −110° C. During WBC participants wore shorts (males) or shorts and vest (females) complemented by gloves, socks, clogs, tubular bandages to cover elbows and knees, headband to cover the ears, and a surgical mask. Local skin temperatures at the chest, posterior upper arm, anterior thigh, and posterior lower leg were measured pre- and post-exposure. Mean skin temperature was calculated as weighted average of the local temperatures.

Simulations of the Hammond protocol, including a 13 minute post-exposure recovery period, were performed with the FPC model using published group-averaged personal characteristics for male and female participants and using clothing configurations as described above. The accuracy of the simulations was assessed by comparing both predicted local and mean skin temperatures with the corresponding means and standard deviations (SD) measured pre- and post-WBC exposure.

Next, WBC experimental trials were conducted by the present inventors using a single-person WPC unit 10 having the features described herein. Six patients (3 female, 3 male) had ages ranging from 18 to 69 years, body height 1.64 to 1.87 m, body mass 55.1 to 81.5 kg, and body fat 15.6 to 34.8% of body mass as estimated from measured skinfold thickness. The six patients underwent a 4 minute WBC exposure to −120° C. in the single-person WPC unit framed by a 15 minute pre-exposure and a 60 minute recovery period at room temperature. They wore only bath clothes and socks during the pre-exposure and recovery period, while during WBC exposure, a headband as ear protection, slippers, mouth cap, and gloves were added.

Core temperature was measured using an ingested radio pill. Skin temperatures were recorded with surface sensors at the neck ($T_{sk,neck}$), scapula ($T_{sk,scapula}$), left hand ($T_{sk,hand}$), and right lower leg ($T_{sk,lower\ leg}$) and were used to calculate mean skin temperature (Tsk,mean) as weighted average according to Eq. (1).

$$T_{sk,mean}=0.28\times(T_{sk,neck}+T_{sk,scapula}+T_{sk,lower\ leg})+0.16\times T_{sk,hand} \quad \text{Eq. (1)}$$

Simulations of these conditions were carried out for each participant using the FPC model adapted to the personal anthropometric and morphological data. Predicted core, mean skin, and local skin temperatures were validated against the measured data. The accuracy of the predictions was assessed using the averaged prediction error (bias) and root-mean squared deviations (rmsd) summary statistics for core and mean skin temperatures computed over the entire duration of the experiment, and for minimum values of mean and local skin temperatures, respectively, representing the actual skin cooling response to WBC.

Following the validation tests described above, parametric simulation studies were performed on the influence of personal characteristics on WBC response. In particular, the FPC model was used to study the influence of individual (personal) characteristics on skin cooling responses to WBC exposure for 3 minutes at −110° C. The parametric simulations were carried out for 36 male and 29 female personal configurations including body height varying from 1.45 to 2.05 m, body mass 45.6 to 129.0 kg, and body fat content from 4.5 to 27.3% of total body mass for males and from 15.0 to 34.7% for females, respectively, thus covering the sex-specific range from athletes to average-population persons up to the limit to obesity.

For further analysis, the following personal characteristics were construed: body height, mass, body surface area (BSA), BSA-to-mass ratio, body fat percentage (BF), lean body mass (wherein LBM=(1−0.01×BF)×mass), body mass index (wherein BMI=mass[kg]/height[m]$^2$), fat free mass index (FFMI=LBM[kg]/height[m]$^2$). The influence of each parameter on predicted skin cooling responses, indicated by the minimum values for both mean and local skin temperatures, was assessed using the goodness-of-fit of linear regression analyses with stepwise variable selection performed separately for both sexes.

Results Compared to Published Data.

Figure 3:
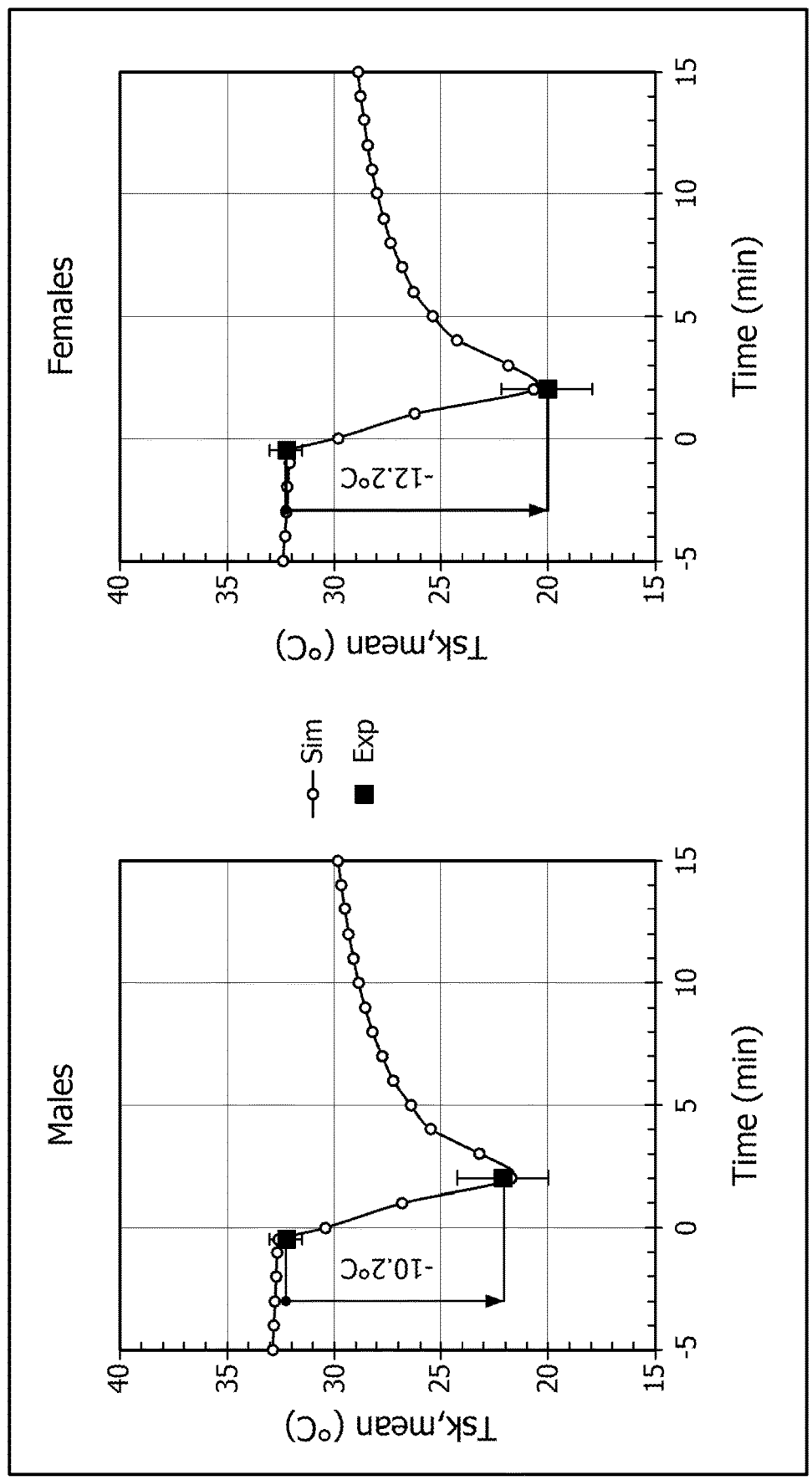
FIG. 3 is a graphical depiction of predicted mean skin temperatures (Sim) for males and females with averaged characteristics compared to means and SD of pre- and post-exposure values (Exp) measured by Hammond.

The predicted mean skin temperatures for both sexes shown in FIG. 3 decreased rapidly after the start of the WBC exposure and reached their minimum at the end of the exposure. On average, females responded to −110° C. by about 2° C. lower mean skin temperature compared to the males who featured over 10% lower body fat content.

Generally, there was a very good agreement between predicted and measured pre- and post-exposure values for the experiment of Hammond, not only for mean skin temperature (FIG. 3), but also for local skin temperatures at chest, upper arm, thigh, and lower leg (not shown). Overall, rmsd was below experimental SD for both pre (0.50 vs. 0.85 K) and post exposure (1.70 vs. 2.32 K), and bias was negligible (pre: 0.09 K; post: 0.01 K). This indicates the suitability of the individualized FPC model to predict skin temperature responses to WBC exposures observed experimentally, including the different responses between males and females.

Results of the Present Experiments.

Figure 4:
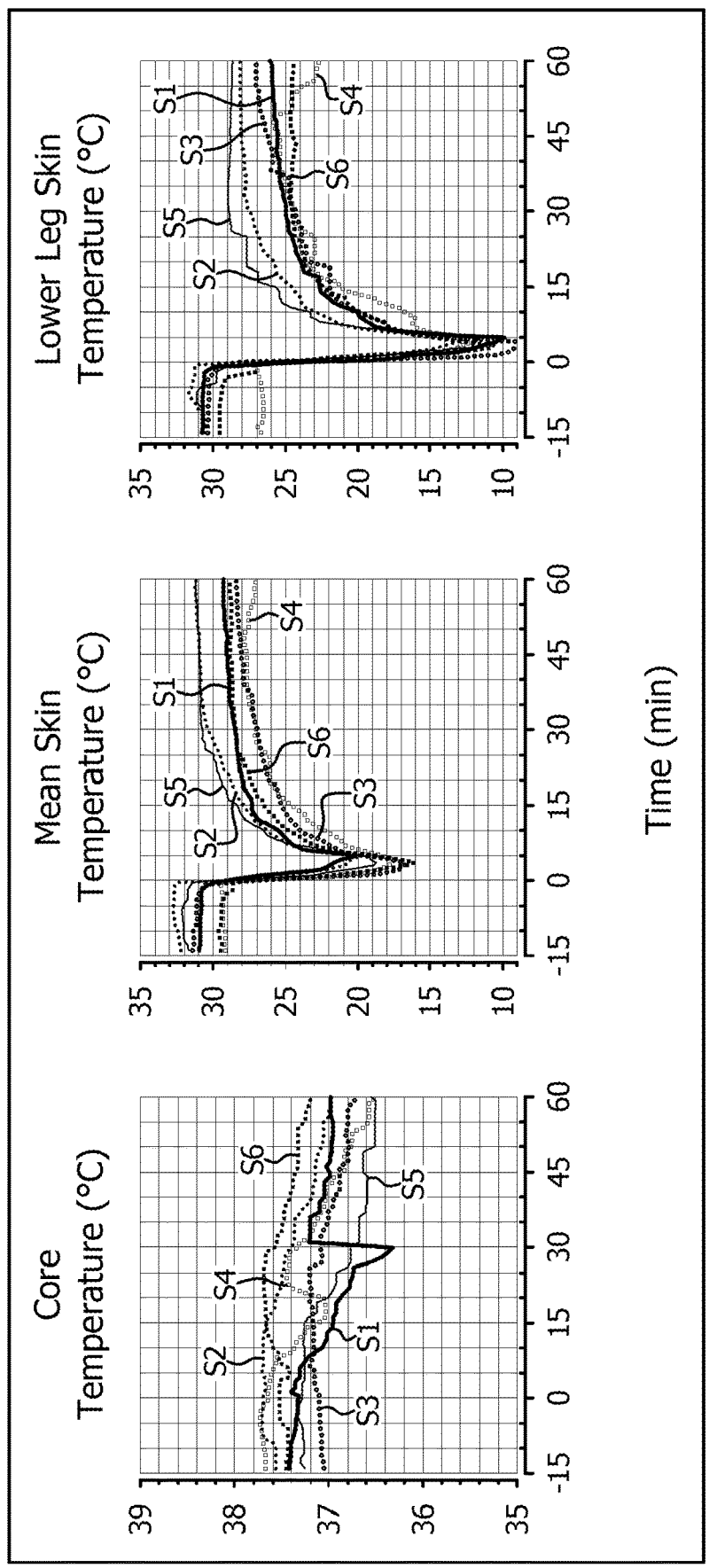
FIG. 4 is a graphical depiction of body core, mean skin and lower leg skin temperatures recorded from six volunteers (S1-S6) before (15-0 min), during (0-4 min), and after (4-60 min) exposure to WBC at −120° C.

There was considerable between-subject variability in the physiological responses to WBC exposure, as depicted in FIG. 4. Nevertheless, several characteristic general patterns emerged including a steady decrease in body core temperature after the start of WBC that continued during the recovery period. In contrast, skin temperatures decreased fast during and reached a minimum at the end of the WBC exposure. Skin temperatures recovered then slowly, but did not reach fully the pre-exposure values, which was in accordance with earlier studies. The lowest local skin temperatures were measured in the lower leg with minimum values 5-10 K below those of mean skin temperature (FIG. 4).

The individualized FPC model predicted very well the course of the core temperature with a negligible bias and rmsd<0.3 K (Table 1). For mean skin temperature over the entire duration including pre-exposure and recovery periods, the predictions agreed to a lower, but still moderate, level of agreement with the measured data with a rmsd<2.0 K (Table 1). Nevertheless, the minimum values representing the actual skin cooling response to WBC of interest were better approximated with slight underestimation bias (−0.4 K) and rmsd<1.5 K for mean skin temperature and rmsd<1 K for lower leg skin temperature (corresponding to 1.5 times experimental SD).

See Table 1.

Also, the level of agreement of measured core and skin temperatures with corresponding predictions using the FPC model was comparable to the outcome of previous validation studies for other scenarios including work in protective clothing under radiant heat load, combined heat stress by temperature and humidity, and widely changing conditions from extreme cold to extreme heat with different activity levels.

TABLE 1

Averaged prediction error (bias) and root-mean squared deviations (rmsd) from FPC simulations of core and mean skin temperatures over the entire duration of the experiment as well as of minimum values of mean and lower leg skin temperatures compared to experimental data from six patients.

| Core temperature | | Mean skin temperature | | Minimum mean skin temperature | | Minimum lower leg skin temperature | |
|---|---|---|---|---|---|---|---|
| bias (K) | rmsd (K) | bias (K) | rmsd (K) | bias (K) | rmsd (K) | bias (K) | rmsd (K) |
| −0.12 | 0.27 | 1.25 | 1.97 | −0.42 | 1.49 | −0.42 | 0.97 |

Figure 5:
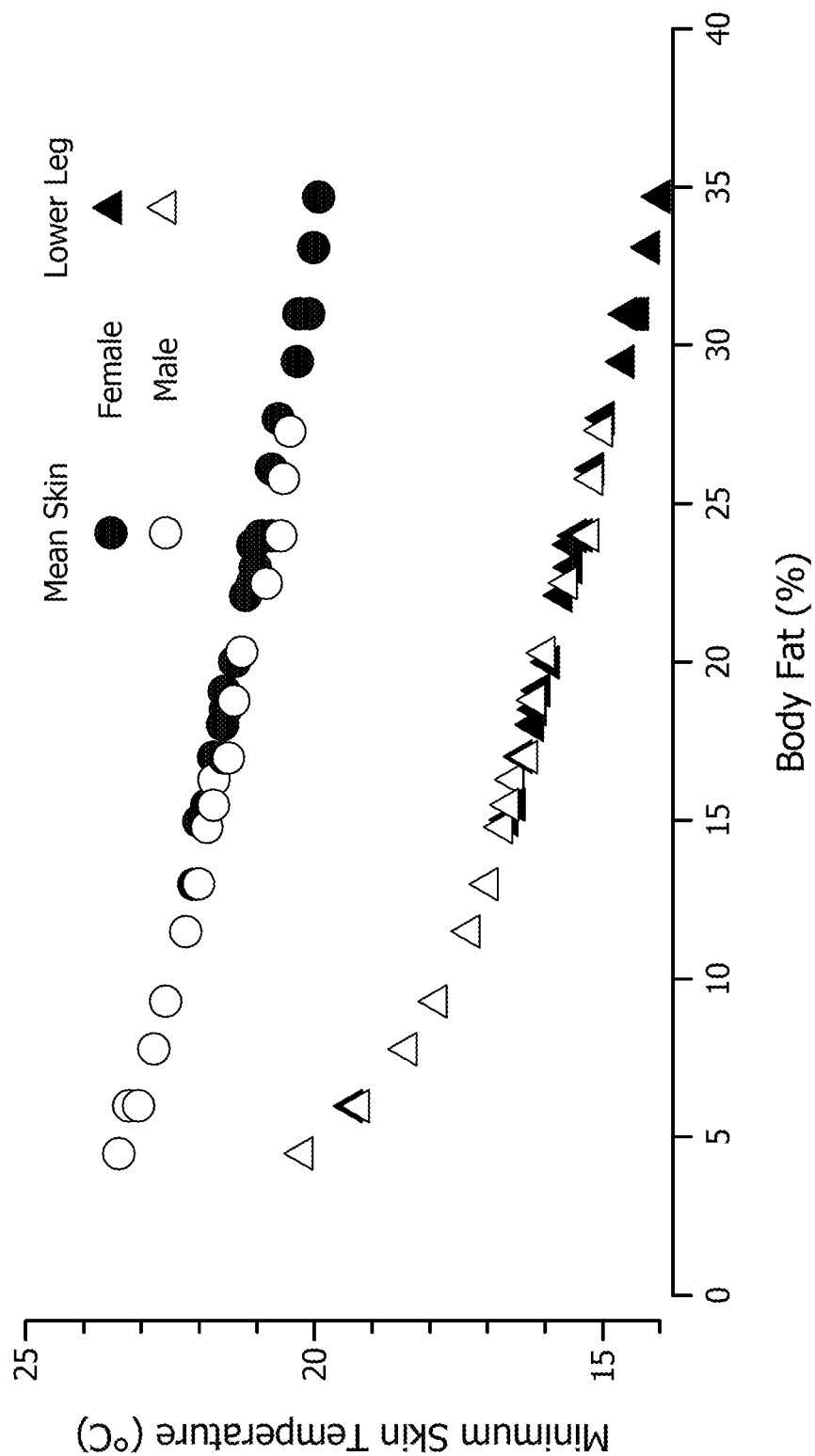
FIG. 5 is a graphical depiction of the correlation between body fat content and the minimum values of mean skin and lower leg skin temperature for both sexes from FPC simulations of 3 min WBC exposure to −110° C.

Among the construed personal characteristics, body fat (BF) showed the highest correlation with the simulated skin cooling response to WBC, indicated by the minimum values, as shown in FIG. 5 for both mean skin and lower leg skin temperatures. Consequently, body fat was involved as independent variable in all linear regressions with stepwise variable selection showing $R^2>0.9$, as summarized in Table 2. This supports the large influence of the body fat content on the cooling response to WBC, as it had also occurred with other tissue cooling modalities.

In case of the minimum mean skin temperature for female configurations and minimum lower leg skin temperature for males, the addition of the fat free mass index (FFMI) and of the interaction term (BF*FFMI) further improved, statistically significantly, the regression models, as indicated by the partial $R^2$ coefficients and corresponding P-values (Table 2). This was in line with results reported by Hammond.

TABLE 2

Goodness-of-fit of linear regressions with stepwise variable selection predicting separately for both sexes the minimum values of both mean skin temperature and lower leg skin temperature by personal characteristics

| Sex | Predicted minimum temperature | Step | Predictor entered | Model $R^2$ | Partial $R^2$ | P-value |
|---|---|---|---|---|---|---|
| female | Mean skin | 1 | BF | 0.9915 | 0.9915 | <.0001 |
| | | 2 | FFMI | 0.9968 | 0.0052 | <.0001 |
| | Lower leg | 1 | BF | 0.9968 | 0.9968 | <.0001 |
| male | Mean skin | 1 | BF | 0.9917 | 0.9917 | <.0001 |
| | Lower leg | 1 | BF | 0.9361 | 0.9361 | <.0001 |
| | | 2 | BF*FFMI | 0.9561 | 0.0200 | 0.0005 |
| | | 3 | FFMI | 0.9825 | 0.0264 | <.0001 |

Summarized, the results of this study showed that the overall and local skin temperature responses to WBC, both of which were always fast though very sensitive to variations in personal characteristics, are well captured by the individualized FPC numerical simulation model. The body fat content and the so-called fat free mass index (FFMI) were found to significantly affect the personal skin temperature response and may thus also affect the protocol settings.

In order to warrant safety and efficacy of whole body cryostimulation applications, human anthropometry and morphology, especially body fat content in combination with the FFMI need to be considered for optimum and safe treatment settings.

Figure 6:
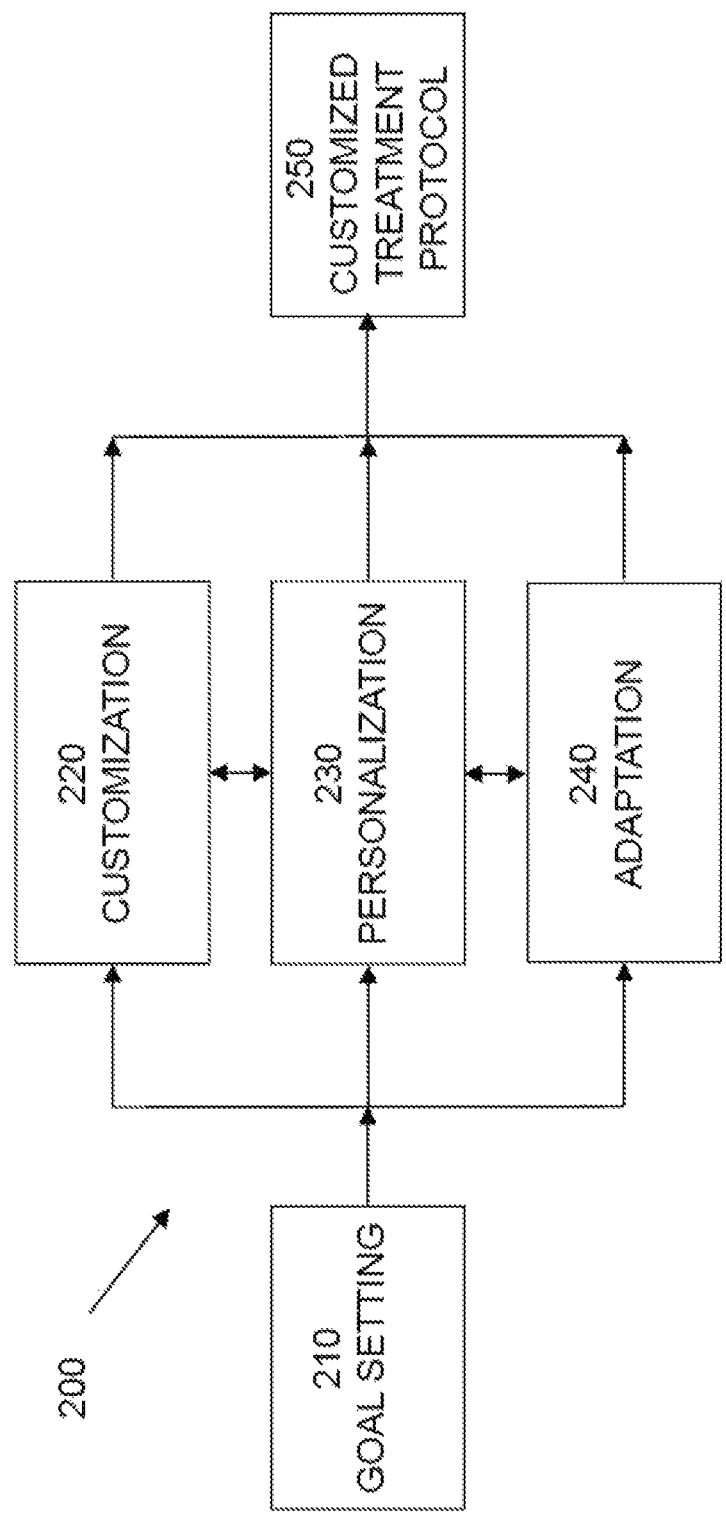
FIG. 6 is a flow chart depicting an exemplary method of delivery customized cryotherapy.

FIG. 6 depicts one embodiment of a method for delivering cryotherapy to a patient using an apparatus as described herein. As describe above, before taking into account the particular characteristics of a patient, the physiological effects of WBC may be affected by treatment duration, treatment temperature, and frequency of treatment, where treatment duration is the time an individual is exposed to WBC, treatment temperature is temperature to which the patient is exposed, and frequency of treatment is the number of treatment protocols a patient has undergone within a particular time frame in relation to it's the purpose for the treatment.

To compare different treatment protocols across various treatment durations and treatment temperatures, it is useful to define a treatment dose as Treatment Dose=1−(Treatment Duration*Treatment Temperature/10000). The physiological effects of treatment can thus be correlated based on this linear relation between treatment duration and treatment temperature (see Table 3), and the treatment dose can be used as a metric for triggering physiological reactions.

TABLE 3

Examples of calculated Treatment Dose based on Treatment Duration and Treatment Temperature.

| Treatment duration (sec) | Treatment temperature (° C.) | Treatment dose |
|---|---|---|
| 120 | −120 | 2.44 |
| 180 | −110 | 2.98 |
| 200 | −130 | 3.60 |

A customized protocol 200, as depicted in FIG. 6, may include up to four steps, it being noted that the steps do not necessarily need to be carried out in the order presented.

Without being bound by theory, to optimize the effects of whole body cryotherapy, evidence suggests that a critical level of tissue cooling must be achieved. The thermal properties of biological tissue mean that it is fundamentally difficult to cool below the skin surface. Subcutaneous adipose tissue (i.e., local fat) has a very low thermal conductivity (0.23 k; by comparison, muscle has a value of 0.46 k), causing it to have an insulating effect on the body. This insulatory effect causes a more significant drop in skin temperatures with higher fat percentages after whole body cryotherapy exposure, i.e., higher fat percentage results in lower skin temperature. Lower skin temperatures result in a difference in biochemical and physiological reactions.

In Step 210, Goal Setting, information is gathered from a patient, typically via an intake interview but alternatively by the patient filling out a form or entering data into a computer. During Goal Setting, the goal and intended treatment benefits to a patient are identified and personal physiological characteristics are assessed. For example, the goal of the treatment may be related to a category such as Sports Care (e.g., recovery, readiness, sleep enhancement, and preparation), Rehab Care (e.g., musculoskeletal disorders, systemic disorders, atopic disorders, and stress), Vitality Care (e.g., quality of life, fitness, sleeps disorders, and general pain relief), or Beauty Care (e.g., anti-aging, skin care, weight-loss, and general well-being). Based on a selected category, a base treatment protocol is selected. Each base treatment protocol consist of a specific description in terms of treatment duration and treatment temperature, together with a description of the treatment frequency and/or treatment cycle (the desired number of treatment protocols within a specific time frame).

In Step 220, Customization, a customization factor is developed for each patient based on three attributes: susceptibility to cold, age, and athletic type (i.e., type of athlete). The customization factor is then apply as a multiplicative correction factor to the protocol specified in Step 210. An initial WBC session is conducted to assess the susceptibility of the patient to cold. In the example presented herein, patient susceptibility is divided into two cold susceptibility categories—regular and high—although a greater number of categories could be found to be useful as more data is collected. The initial WBC session involves subjecting a patient to a relatively mild treatment temperature (for example, −80° C. to about −100° C., and preferably about −90° C.) for a relatively short treatment duration (for example, about 1.5 minutes to about 2.5 minutes, and preferably about 2 minutes). During this first mild treatment protocol, a patient's autonomic response, comfort, and personal reaction to the thermal sensation are assessed. This determines a personal adaptation curve and defines the optimal starting point for a patient's treatment.

Patients are divided into a plurality of intensity categories based on age. In the example shown in Table 4, an exemplary set of intensity categories are: High (the highest intensity group for patients 18 to 35 years); Severe (a mid-level intensity group for patients 35 to 55 years); and Moderate (a lower intensity group for patients under 18 years and over 55 years). In Table 4, a fourth category, (Low) is made available for a patient desiring or requiring a less intense treatment.

Patients are also divided into a plurality of categories based on type of athlete, to take into account differences in anthropometrics. In the example show in Table 4, three athlete type categories are used: Recreational (participates in sports on a recreational level up to 6 hours per week); Competitive (participates in sports on a competitive level, 6 to 18 hours per week) I and Elite (participates in sports on a professional level for more than 18 hours per week).

TABLE 4

A tabulation of the customization factor determined to account for the cold susceptibility, age, and type of athlete.

| | Recreational | Competitive | Elite | Elite | Competitive | Recreational |
|---|---|---|---|---|---|---|
| (Low) | 0.91 | 0.93 | 0.95 | High cold susceptibility | | |
| Moderate | 0.93 | 0.95 | 0.97 | | | |
| Severe | 0.96 | 0.98 | 1 | | | |
| High | 0.98 | | 1.02 | | | |
| High | Regular cold susceptibility | | | 1.0 | 0.98 | 0.96 |
| Severe | | | | 0.98 | 0.96 | 0.94 |
| Moderate | | | | 0.95 | 0.93 | 0.91 |
| (Low) | | | | 0.93 | 0.91 | 0.89 |

The customization factor is applied to the base protocol treatment dose, essentially acting as a dampening factor in relation to safety. For example, an elite athlete, being 27 years old and regularly susceptible to cold, has a customization factor of 1.02. In case the standard WBC protocol (e.g., 3 minutes at −110° C.) having a treatment dose of 2.98, this dose would be multiplied by 1.02 resulting in a customized treatment dose of 3.04, implying an extension of the protocol of 5 seconds. The treatment protocol of 3 minutes and 5 seconds at −110° C. may be further adjusted based on a personalization for individual characteristics in Step 230.

In Step 230, Personalization, a patient's individual characteristics are taken into account and the treatment protocol is adjusted accordingly. These characteristics may include, but are not limited to, the patient's height, mass, body surface area (BSA), BSA-to-mass ratio, body fat percentage (BF), lean body mass (LBM), body mass index (BMI), and fat free mass index (FFMI). In the example above, if the athlete is 193 cm in height and 83 kg in mass and a body fat percentage of 13%, a personalization factor of 11 seconds would be indicated, resulting in a revised treatment duration of 3 minutes and 16 seconds at −110° C. Note that because both the customization factor and the personalization factor are additive or corrective to the base treatment protocol, Steps 220 and 230 may be reversed in order if desired.

In Step 240, Adaptation, and adaption factor is determined and applied based on the treatment frequency or treatment cycle. Basically, the adaptation factor increases the intensity of the treatment protocol as tolerance increases. One means to accomplish this would be to increase the treatment intensity by using an adaptation factor of 2° C. for every other treatment of a patient. For example, the treatment temperature of a protocol would be decrease from −125° C. to −135° C. after 20 exposures (to take into account the impact of a series of treatments). As with Steps 220 and 230, it is understood that the adaptation factor can be applied before or after one or both of the customization factor and personalization factor to yield the same net result.

In Step 250, the combined application of the customization factor, the personalization factor, and the adaptation factor applied to the base treatment protocol as determined by the Goal Setting Step 210 result in a Customized Treatment Protocol which is then used to treat a patient.

It should be noted that one or more of the customization factor, the personalization factor, and the adaptation factor are based on a reference person. In one embodiment, the reference person is a specific Olympic-level athlete. In other embodiments, the reference person may be selected to be similar to the patient being treated, for example in developing a treatment protocol for a bicyclist or for a boxer, a professional cyclist or boxer, respectively, may be used as the reference person. Alternatively, or in combination with the foregoing, the reference person may be a composite of two or more athletes who may be the same or different types of athletes.

The present invention is not to be limited in scope by the specific aspects or embodiments disclosed in the examples which are intended as illustrations of a few aspects of the invention and any embodiments that are functionally equivalent are within the scope of this invention. Various modifications of the invention in addition to those shown and described herein will become apparent to those skilled in the art and are intended to fall within the scope of the appended claims.

The invention claimed is:

1. A cryotherapy apparatus comprising:
a heat exchanger mounted in an exchanger enclosure;
a cryotherapy chamber configured to receive at least a portion of a body of a patient designated to receive cryotherapy;
a nitrogen supply conduit configured to supply cryogenic nitrogen to the heat exchanger;
a nitrogen exhaust conduit configured to exhaust nitrogen from the heat exchanger;
an air return conduit configured to flow warmed return air from the cryotherapy chamber to the heat exchanger enclosure;
an air supply conduit configured to flow chilled air from the heat exchanger enclosure to the cryotherapy chamber;
a variable speed fan configured to cause a flow rate of chilled air through a loop including the air return conduit, the heat exchanger, the air supply conduit, and the cryotherapy chamber; and
a controller programmed to control the flow rate of chilled air to the cryotherapy chamber by regulating the speed of the variable speed fan according to a treatment protocol; and to selectively direct the chilled air to one or more selected portions of the body of a patient designated to receive cryotherapy, and to control the flow rate of the chilled air to the one or more selected portions of the human body;
wherein the controller is further programmed to provide customized treatment protocols based on one or more of: a characteristic of the patient being treated, a type of treatment required, a type of injury being treated, a type of athletic activity from which recovery is desired, and a portion of the body requiring treatment;
wherein the controller is programmed to provide customized treatment protocols taking into account one or more of: a patient's treatment goals, a customization factor, a personalization factor, and an adaptation factor;
wherein the customization factor takes into account one or more of a patient's cold susceptibility, a patient's age, and a patient's athletic type;
wherein the personalization factor takes into account one or more of a patient's body height, mass, surface area, body surface area-to-mass ratio, body fat percentage, lean body mass, body mass index, and fat free mass index;
wherein the adaptation factor takes into account a one or both of treatment frequency and a treatment cycle; and
wherein the controller is programmed to provide customized treatment protocols by calculating one or more of the patient's treatment goals, the customization factor, the personalization factor, and the adaptation factor based on a reference athlete.

2. The cryotherapy apparatus of claim 1, wherein the fan is a reversible fan configured to enable a flow rate of chilled air through the loop in either direction.

3. The cryotherapy apparatus of claim 1, further comprising a control valve in the nitrogen supply conduit to regulate the supply of cryogenic nitrogen, wherein the controller is further programmed to control the supply of cryogenic nitrogen according to a treatment protocol.

4. The cryotherapy apparatus of claim 1, further comprising a temperature sensor positioned to sense a return air temperature, wherein the controller is further programmed to control the flow rate of air based at least on part on the return air temperature.

5. The cryotherapy apparatus of claim 1, further comprising a condensate drain positioned at a low point in the air return conduit for removing condensation formed in one or both of the exchanger enclosure and the cryotherapy chamber.

6. The cryotherapy apparatus of claim 1, further comprising a temperature sensor to sense a nitrogen exhaust temperature, wherein the controller is further programmed to shut off liquid nitrogen supply if the nitrogen outlet temperature is at or below a preset limit.

7. The cryotherapy apparatus of claim 1, further comprising a heater in the air return conduit for heating the recirculating air to enable defrosting of the cryotherapy chamber.

8. The cryotherapy apparatus of claim 1, wherein the controller is programmed to provide customized treatment protocols taking into account a patient's treatment goals.

9. The cryotherapy apparatus of claim 1, wherein the controller is programmed to provide customized treatment protocols taking into account a customization factor based one or more of a patient's susceptibility to cold, age, and athletic type.

10. The cryotherapy apparatus of claim 1, wherein the controller is programmed to provide customized treatment protocols taking into account a personalization factor based on one or more of a patient's body height, mass, surface area, body surface area-to-mass ratio, body fat percentage, lean body mass, body mass index, and fat free mass index.

11. The cryotherapy apparatus of claim 1, wherein the controller is programmed to provide customized treatment protocols taking into account an adaptation factor based on one or both of treatment frequency and a treatment cycle.

12. The cryotherapy apparatus of claim 1, wherein the customized treatment protocols enable customization of a portion of the body being treated, exposure times, timed cycles, exposure temperatures, temperature cycles, cold intensity, and cold intensity cycles.

13. The cryotherapy apparatus of claim 1, wherein the chilled air flow rate is controlled to provide a treatment temperature from −150° C. to −90° C.

14. The cryotherapy apparatus of claim 1, wherein the chilled air flow rate is controlled to provide a treatment temperature from −135° C. to −110° C.

15. The cryotherapy apparatus of claim 1, wherein the chilled air flow is controlled to provide a heat transfer effect from $5W/m^2$ ° C. to $100W/m^2$ ° C.

16. A method of delivering cryotherapy using a cryotherapy chamber as in claim 1 configured to receive at least a portion of a human body designated to receive cryotherapy, the method comprising:
- recirculating air in a loop through a heat exchanger, into the cryotherapy chamber, and out form the cryotherapy chamber, and returning to the heat exchanger;
- chilling the air to a therapeutic chilled air temperature in the heat exchanger by heat exchange with liquid nitrogen; and
- operating the cryotherapy chamber according to a customized treatment protocol comprising controlling the flow rate of the chilled air.

* * * * *